United States Patent [19]
Ginsburg

[11] Patent Number: 5,969,792
[45] Date of Patent: Oct. 19, 1999

[54] VARIABLE LUMINANCE CONTRAST SENSITIVITY AND GLARE VISION TEST PROCESS

[76] Inventor: Arthur Ginsburg, 1973 Robin Ridge Ct., Walnut Creek, Calif. 94596

[21] Appl. No.: 09/075,386

[22] Filed: May 8, 1998

[51] Int. Cl.$^6$ .................................................. G03B 17/00
[52] U.S. Cl. ............................................................. 351/243
[58] Field of Search .................................. 351/239, 243, 351/244, 246, 222

[56] References Cited

U.S. PATENT DOCUMENTS

| | | | |
|---|---|---|---|
| 4,800,404 | 1/1989 | Ginsburg et al. | 351/243 |
| 5,471,262 | 11/1995 | Trokel | 351/239 |
| 5,550,602 | 8/1996 | Braeuning | 351/243 |

*Primary Examiner*—George Manuel
*Attorney, Agent, or Firm*—Townsend and Townsend and Crew LLP

[57] ABSTRACT

A process for testing vision sensitivity from a target is set forth. Specifically, I illuminate the vision sensitivity chart with only indirect light and in the total absence of direct light. In the preferred embodiment, the contrast sensitivity chart is placed in an enclosure and provided with only indirect illumination of a desired intensity. The indirect illumination is such that all light illuminating the vision sensitivity target first indirectly rebounds from a surface and only then is incident upon the vision sensitivity target. At the same time, light rays on the target from this illumination cannot directly rebound into the direct viewer of the subject being tested. With an enclosure having this characteristic, paired viewing apertures are provided and spaced from the eye to provide the eye with a clear the contrast sensitivity chart. Offset from the eye and at a solid angle emulating a real life night driving light source, such as a headlight, light having a direct glare is introduced to the eye. Thereafter, for various indirect light levels on the contrast sensitivity chart, measurements are made with and without glare from the glare sources being present. The test results have been found by me to reliably predict test results on my prior art simulator enabling a simple clinical analog to take the place of what heretofore was much more elaborate testing.

5 Claims, 3 Drawing Sheets

VARIABLE LUMINANCE CONTRAST SENSITIVITY AND GLARE VISION TEST PROCESS

This invention relates to the testing of contrast sensitivity. More particularly, a method of testing night vision is disclosed in which a contrast sensitivity chart is only indirectly illuminated while glare is directly introduced to the eye. By comparing vision contrast sensitivity in the absence of glare to vision contrast sensitivity in the presence of glare, I have found that a direct correlation exists between a simple static testing and actual real world night vision visibility conditions.

BACKGROUND OF THE INVENTION

I have developed, and it is prior art to this invention, a night time vision sensitivity testing simulator. This simulator includes the subject sitting behind the wheel of a sectioned car having a conventional windshield and driving interior. Through the windshield of the sectioned car, an observer views, projected by video or movie, a real world night driving scene. In my preferred embodiment I used a "country" night driving scene and a "city" night driving scene. The scenes are motion scenes with the driver seeing various road signs and hazards as if the car is proceeding at normal driving speeds (55 mph in the country and 35 mph in the city). To provide the equivalent of real world glare, I added glare sources to the simulator. Specifically, I attached small lights to the rear view mirror and the side view mirror. The solid angle of the source of the lights was maintained to produce an equivalent to an automobile headlight shining either through the side or rear view mirror. Naturally, this glare reproduced by reflection substantially the same glare as that of an on coming car.

Under these conditions, the effect of glare was measure by having the patient push a mechanical indicator whenever a road sign or hazard was identified. Upon pushing of the mechanical indicator, the sign or hazard was blanked out, and the patient asked to designate with particularity the sign or hazard observed. Sensitivity in the simulator was judged by the projected distance at which the subject undergoing test observed the sign or hazard.

Vision sensitivity was formerly measured with Snellen charts, the familiar randomly placed letters which diminish in size along graduated visual sensitivity lines. The subject in reading one line of larger letters can be graded 20/30, the next line of smaller letters 20/20, etc.

In U.S. Pat. No. 5,414,479 issued May 9, 1996 and U.S. Pat. No. 5,500,699 issued Mar. 3, 1996 both entitled Spatial Frequency and Contrast Sensitivity Test Chart and Method, I have shown that by using fine gradations of lines on a chart, contrast vision sensitivity can be more accurately determined. Additionally, and in U.S. Pat. No. 5,500,699 issued Mar. 3, 1996 both entitled Spatial Frequency and Contrast Sensitivity Test Chart and Method, I have shown that the background provided such images is necessary to avoid image artifacts that may otherwise be generated to provide in accurate or misleading test results. It will be understood that these issued patents form the preferred targets utilized with this disclosure, although the prior art Snellen tests or other low or high contrast vision sensitivity tests may be used as well.

Accordingly, these patents are incorporated by reference to this disclosure as if set forth herein in full.

DISCOVERY

As can be seen from the above description, my sectioned car night vision testing device was and is an elaborate and expensive real world projection device. It is not practical for clinical usage.

Using results from this more elaborate device, I have experimented with a simplified vision contrast sensitivity testing apparatus herein disclosed. These experiments have included the clinical deployment of the vision testing apparatus and gathering data from a population of subjects at ten clinical locations. Only after this data was gathered and analyzed was I able to establish definitively a correlation between data gather on my sectioned night vision simulator and date gathered on my vision sensitivity testing device. The reader is advised that the experimental usage of this device occurred more than one year before the filing of this patent application.

This simplified vision sensitivity process tests vision sensitivity with and without the presence of glare. I have recently discovered that the results from this testing process correlate with the results of my earlier, more expensive and elaborate sectioned car night vision testing device. The reader will also understand that before a process can be reduced to clinical practice, the clinical efficacy of that process must be thoroughly established.

SUMMARY OF THE INVENTION

A process for testing vision sensitivity from a target is set forth. While a regular (Snellen) vision sensitivity chart may be used, I prefer a vision contrast sensitivity chart such as that set forth and described in my U.S. Pat. No. 5,500,699 issued Mar. 3, 1996 both entitled Spatial Frequency and Contrast Sensitivity Test Chart and Method. Specifically, I illuminate the vision sensitivity chart with only indirect light and in the total absence of direct light. In the preferred embodiment, the contrast sensitivity chart is placed in an enclosure and provided with only indirect illumination of a desired intensity. The indirect illumination is such that all light illuminating the vision sensitivity target first indirectly rebounds from a surface and only then is incident upon the vision sensitivity target. At the same time, light rays on the target from this illumination cannot directly rebound into the direct viewer of the subject being tested. With an enclosure having this characteristic, paired viewing apertures are provided and spaced from the eye to provide the eye with a clear view of the contrast sensitivity chart. Offset from the eye and at a solid angle emulating a real life night driving light source, such as a headlight in the rear view and/or side view mirror, light having a direct or side glare is introduce to the eye. Thereafter, for various indirect light levels on the contrast sensitivity chart, measurements are made with and without various direct glare inputs from the glare sources being present. The test results have been found by me to reliably predict test results on my prior art simulator enabling a simple clinical analog to take the place of what heretofore was much more elaborate testing.

I use the term "indirect light" as a limitation to this invention. To obtain this "indirect light", I position the light source with respect to the eye so that no portion of the light emanating from the source can be reflected by the vision sensitivity testing chart to directly the eye. All light from the source first is incident to some other surface than the vision sensitivity source. At the same time, direct light rays rebounding from a first surface of incidence to the vision sensitivity target, rebound from the target along a path that is not directly incident to the eye. Thus, the term "indirect light" is to be narrowly construed.

It is an advantage of the disclosed vision testing process that no glare results from the vision sensitivity target. This is to be contrasted with my night time vision sensitivity testing simulator. This simulator relies on image projection.

Where an image is projected, some glare from the test image is introduced to the night viewers vision. The light projected to create the image can directly rebound from the image directly to the viewers eye. Thus, outside of the glare sources attached to the side and rear view mirrors, some glare is inevitably introduced by the process of image projection.

DESCRIPTION OF THE PREFERRED EMBODIMENT

Figure 1:
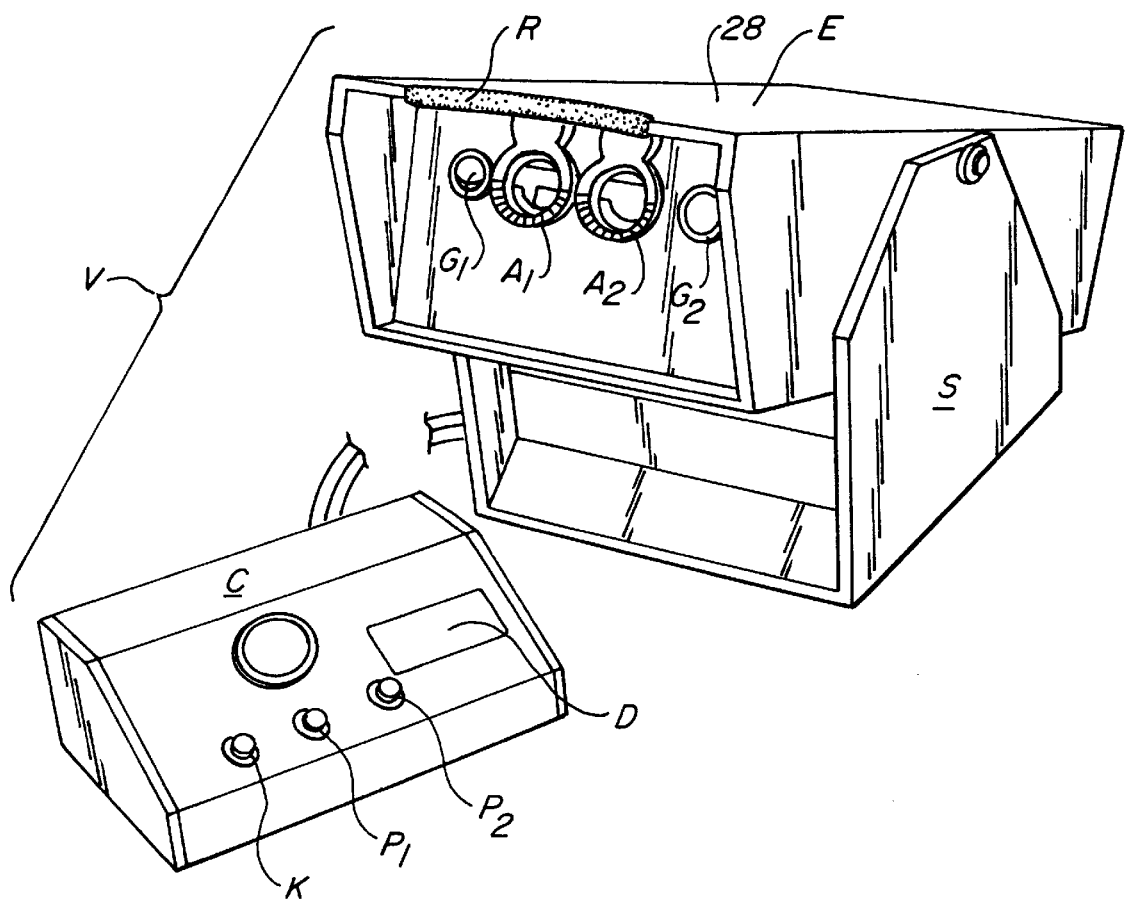
FIG. 1 is a perspective view of the night vision eye test equipment used to gather the data for this testing process.

Referring to FIG. 1, a perspective view of the vision test apparatus used to acquire the data is illustrated. Vision tester V includes luminance controller C and vision testing enclosure E. Vision testing enclosure E illustrates left eye aperture $A_1$ and right eye aperture $A_2$. Adjacent left eye aperture $A_1$ is right eye glare aperture $G_1$; similarly adjacent right eye aperture $A_2$ is right eye glare aperture $G_2$. Lenses $L_1$ and $L_2$ are lenses placed to create distance vision.

Typically, vision tester V is table mounted; accordingly it is provide with stand S that permits pivotal turning about a horizontal axis to enable sitting subjects of all sizes to be tested. In testing, subject Q (see FIG. 3) places his forehead against head rest R and views vision sensitivity target T on rear wall 18 of vision testing enclosure E (see FIG. 2).

Luminance controller C includes essentially three potentiometer. Indirect illumination potentiometer K controls the intensity of indirect light bulb B interior of vision testing enclosure E (shown in FIG. 2 and 3). Left eye glare potentiometer $P_1$ controls left eye glare light source 14; right eye glare potentiometer $P_2$ controls right eye glare source 16. Display D enables the intensity of the lights to be displayed; indirect light bulb B in foot lamberts and left and right eye glare light source 14 and 16 in lux. These controls are conventionally designed and calibrated.

Figure 2:
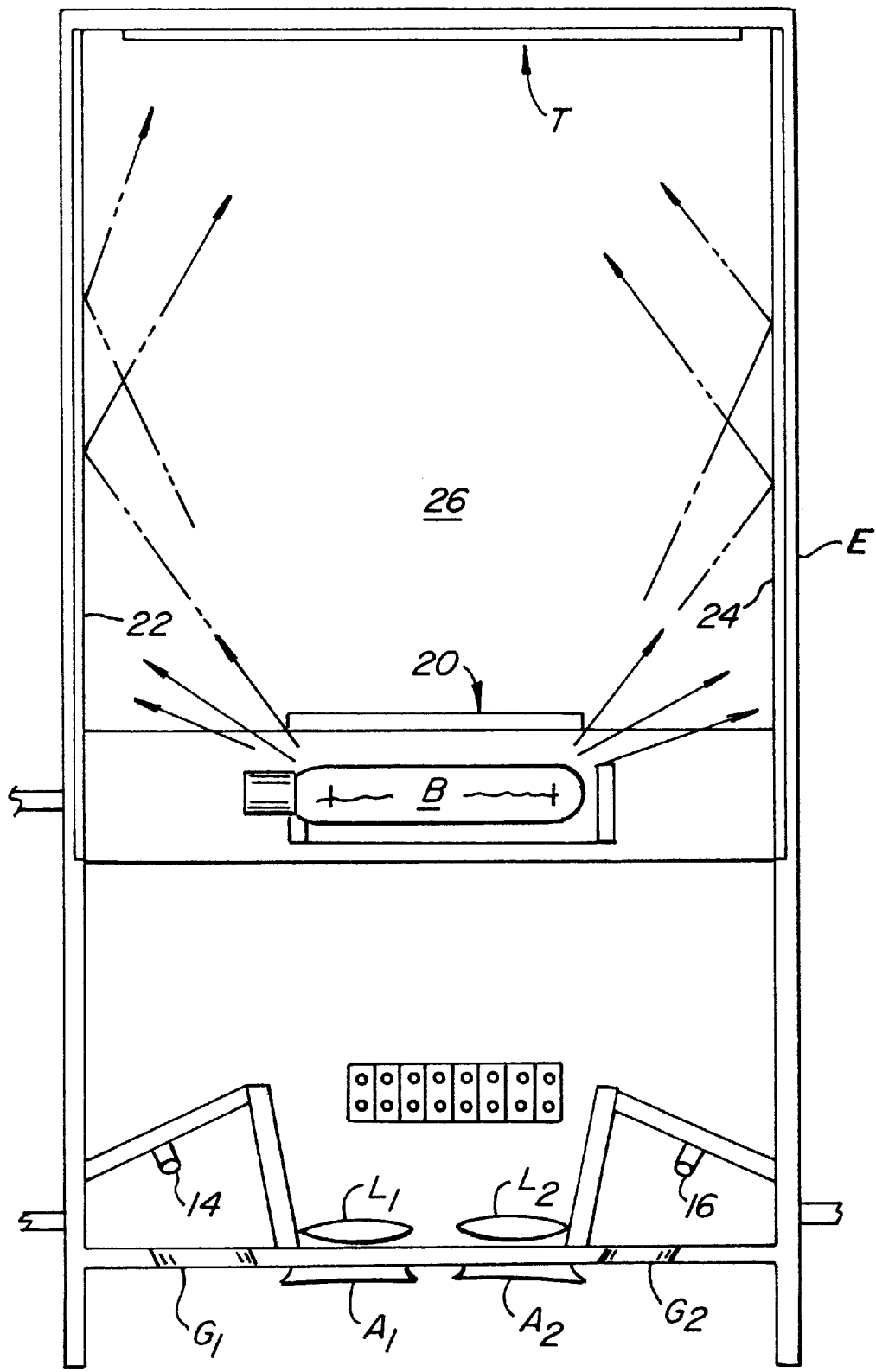
FIG. 2 is a top plan view of the testing device of FIG. 1 illustrating respectively the indirect light source for illuminating the contrast sensitivity target and the direct light sources for emulating direct side glare to the subject undergoing testing.

Referring to FIG. 2, the interior baffling of vision testing enclosure E can be seen and understood in the sectioning provided. First, indirect light bulb B is provided with shielding 20. This shielding 20 completely surrounds indirect light bulb B to produce two conditions from the light emanating from the bulb. First, all light incident on vision sensitivity target T is indirectly reflected off top wall 28 (see FIG. 1), side walls 22 and 24 or bottom wall 26. For the purposes of producing the optimum reflection, these respective walls are covered with dull white plastic material.

Second, and when the light is directly incident from side walls 22 and 24, bottom wall 26 or top wall 28 onto target T, light having a direct angle of reflection, parallel to and at an opposite angle from light incident on the target T, cannot have a direct incident path to the eye of the viewer. It will be understood that highly illuminated surfaces can be the source of their own glare. I avoid this secondary glare by providing a flat target T and making sure that the angle of reflection of the indirectly illuminating light cannot find a direct path of illumination to the viewer, this source of secondary glare is prevented.

Figure 3:
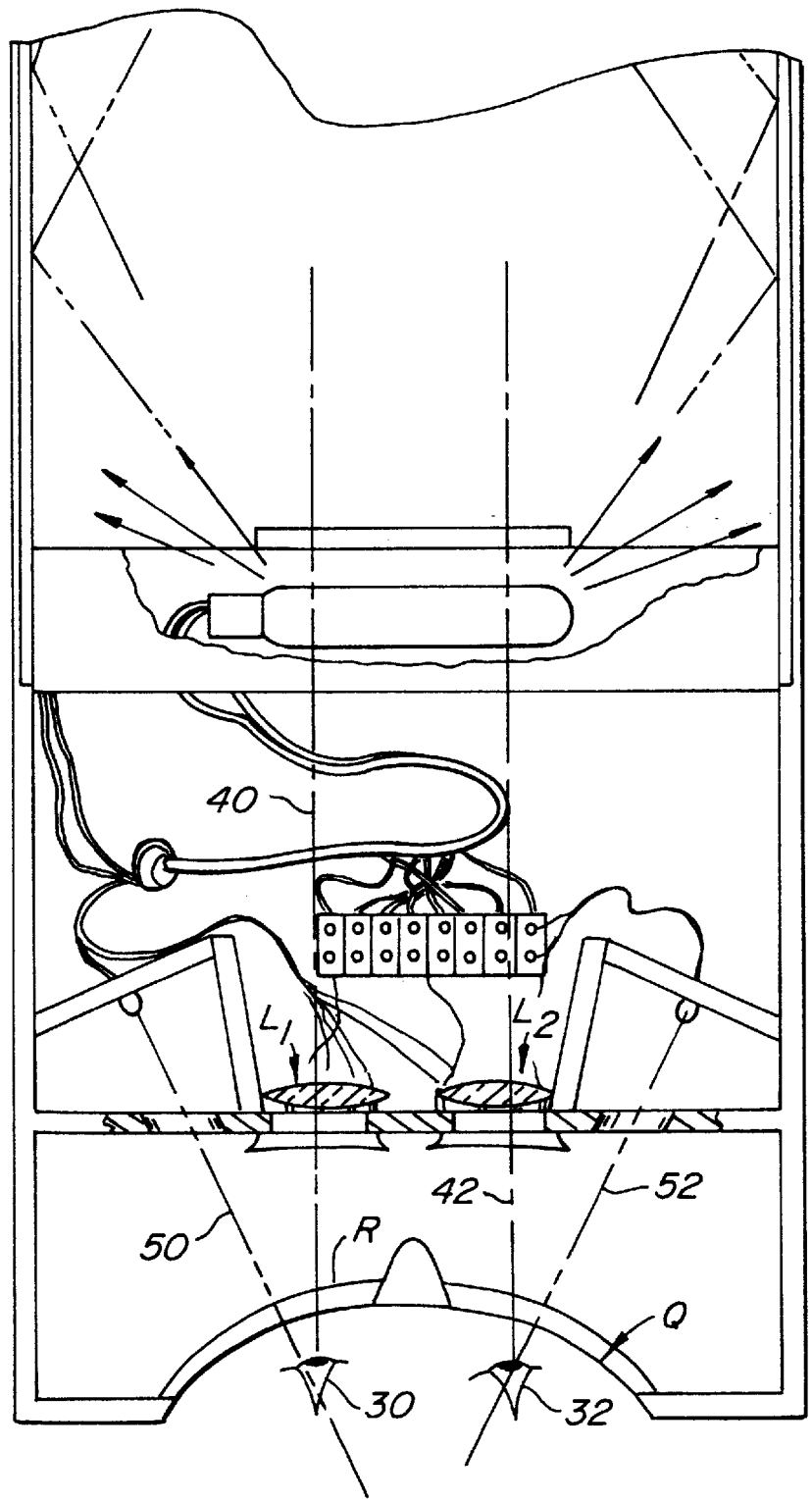
FIG. 3 is a view similar to FIG. 2, illustrating a subject viewing the contrast sensitivity source with direct glare being added.

Referring to FIG. 3, left eye glare light source 14 as it relates to left eye glare aperture $G_1$ and right eye glare source 16 as it relates to right eye glare aperture $G_2$ can be understood. Specifically, head rest R is placed with respect to left eye aperture $A_1$ and right eye aperture $A_2$ so that left eye 30 and right eye 32 are at the rough intersection of target line of sight 40 and 42 through lenses $L_1$ and $L_2$ and glare source lines of sight 50 and 52. Thus, the patient—while looking straight ahead and determining whether sufficient vision sensitivity results from vision sensitivity target T can have glare from each light source introduced to his eye.

Mention must be made about the relative size of left eye glare light source 14 and right eye glare source 16. Specifically, these respective lights have a solid angle of view as viewed from left eye 30 and right eye 32 respectively to emulate an automobile headlight. As I have observed that the glare produced either by offset direct head on view and reflected rear and side mirror view are approximately the same, the placement of these light sources approximating the rear view mirrors of a car have all been found to be equivalent to night headlight glare conditions.

Having set forth the general construction of the device disclosed, I can now set forth the parameters of a typical test. By appropriate adjustment of indirect illumination potentiometer K, I bring indirect light bulb B to an intensity where vision sensitivity target T is illuminated by 0.8 foot lamberts. Similarly, by appropriate adjustment of left eye glare potentiometer $P_1$ and right eye glare potentiometer $P^2$, respective left eye glare light source 14 and right eye glare source 16 are brought to emanate 35 to 36 lux. Thereafter, and using vision sensitivity target T similar to FIG. 4 or 5 of U.S. Pat. No. 5,414, 479 vision contrast sensitivity of patients are measured.

In making such vision contrast sensitivity measurements over a wide population of patients, I have discovered that the measurements obtained utilizing this simple device directly correlate to both emulated night vision visibility conditions as described in my night time vision sensitivity testing simulator or in actual viewing conditions.

What is claimed is:

1. A process of testing night vision with glare from an eye of a subject being tested comprising the steps of:

providing a vision sensitivity target;

placing the vision sensitivity target in an enclosed environment;

providing at least one a viewing aperture into the enclosed environment to provide a view of the vision sensitivity target from across the enclosed environment;

illuminating the vision sensitivity target from a light source with only indirect light and in absence of direct light by rebounding light from the enclosed environment onto the vision sensitivity target and having such rebounding light have no path of direct incidence to the eye of the subject being tested;

providing a viewing station remote from the at least one viewing aperture to provide the eye with a clear angle of view;

providing at least one glare source to the eye having a solid angle of origin emulating a night light source from a headlight of a vehicle reflected in a side and/or rear view mirror;

testing vision sensitivity in absence of direct glare to the eye; and, testing vision sensitivity in the presence of glare from the at least one glare source.

2. The process of testing night vision with glare according to claim 1 and wherein the step of providing a vision sensitivity target includes providing a vision contrast sensitivity target.

3. The process of testing night vision with glare according to claim 1 and wherein the step of providing at least one a viewing aperture into the enclosed environment includes providing two viewing apertures into the enclosed environment.

4. The process of testing night vision with glare according to claim 1 and wherein the step of illuminating the vision sensitivity target from a light source includes indirectly illuminating the vision sensitivity target from a light source having variable intensity.

5. The process of testing night vision with glare according to claim 1 and wherein the step of providing at least one glare source to the eye includes providing a variable glare source to the eye emulating side and/or rear view mirror glare.

* * * * *